(12) United States Patent
Cui

(10) Patent No.: US 11,224,885 B2
(45) Date of Patent: Jan. 18, 2022

(54) FOGGER

(71) Applicant: Foshan Naibao Electric Co., Ltd., Guangdong (CN)

(72) Inventor: Jiayao Cui, Guangdong (CN)

(73) Assignee: Foshan Naibao Electric Co., Ltd.

( * ) Notice: Subject to any disclaimer, the term of this patent is extended or adjusted under 35 U.S.C. 154(b) by 0 days.

(21) Appl. No.: 16/990,145

(22) Filed: Aug. 11, 2020

(65) Prior Publication Data

US 2021/0053078 A1 Feb. 25, 2021

(30) Foreign Application Priority Data

Aug. 22, 2019 (CN) .......................... 201921375896.6

(51) Int. Cl.
| | |
|---|---|
| *B01F 3/04* | (2006.01) |
| *B05B 7/04* | (2006.01) |
| *B01F 5/04* | (2006.01) |
| *B01F 15/02* | (2006.01) |
| *B05B 7/00* | (2006.01) |

(52) U.S. Cl.
CPC ........ *B05B 7/0416* (2013.01); *B01F 3/04049* (2013.01); *B01F 3/04056* (2013.01); *B01F 5/0461* (2013.01); *B01F 15/0203* (2013.01); *B01F 15/0262* (2013.01); *B05B 7/0081* (2013.01); *B01F 2215/0091* (2013.01)

(58) Field of Classification Search
CPC .... B01F 3/04; B01F 3/04056; B01F 3/04049; B05B 7/0416
See application file for complete search history.

(56) References Cited

U.S. PATENT DOCUMENTS 8,636,231 B2 * 1/2014 Rosario ..................... B05B 7/26
239/419

* cited by examiner

*Primary Examiner* — Robert A Hopkins
(74) *Attorney, Agent, or Firm* — Lerner, David, Littenberg, Krumholz & Mentlik, LLP

(57) ABSTRACT

The present utility model relates to a fogger, comprising: a casing with an air suction inlet and a spray port; an air duct assembly located in the said casing, wherein the air duct assembly includes an air duct shell and a fan, of which the said air duct shell has an air inlet, an air outlet, and an air duct that connects the said air inlet and the said air outlet, and the said fan is located in the said air duct; the said air inlet is connected to the said air suction inlet, the said air outlet is connected to the said spray port; and a liquid storage tank located in the said casing, wherein the liquid storage tank delivers liquid to the said spray port via a liquid delivery tube, and the said air duct is connected to the said liquid storage tank via an air delivery tube. A fogger of the present utility model can effectively improve the convenience of use.

10 Claims, 5 Drawing Sheets

FOGGER

CROSS-REFERENCE TO RELATED APPLICATIONS

The present application claims priority from Chinese Patent Application No. 201921375896.6 filed Aug. 22, 2019, the disclosure of which is hereby incorporated herein by reference.

TECHNICAL FIELD

The present utility model relates to the field of spray equipment, and in particular to a sprayer.

BACKGROUND ART

A fogger is a device that can disperse liquid into mist droplets, and it can be widely used in scenarios such as insecticides, disinfection, humidification or cooling. For example, in some residences, shopping malls or exhibitions, foggers are often used as insecticidal and disinfection devices to improve the quality of the environment and enhance the comfort level of the environment. Traditional foggers usually need to be connected to an external liquid delivery tube, which takes up a large space. In addition, they can only be used at fixed locations and cannot be moved freely, which makes the use of the fogger inconvenient.

Summary of Utility Model

Based on this, it is necessary to provide a type of fogger that can help overcome the inconvenience of using traditional foggers.

A fogger, comprising:

a casing with an air suction inlet and a spray port;

an air duct assembly located in the said casing, wherein the air duct assembly includes an air duct shell and a fan, of which the said air duct shell has an air inlet, an air outlet, and an air duct that connects the said air inlet and the said air outlet, and the said fan is located in the air duct; the said air inlet is connected to the said air suction inlet, the said air outlet is connected to the said spray port; and a liquid storage tank located in the said casing, wherein the liquid storage tank delivers liquid to the said spray port via a liquid delivery tube, and the said air duct is connected to the liquid storage tank via an air delivery tube.

The aforementioned fogger uses the fan to suck air from the outside into the casing via the air suction inlet, and the air flows into the air duct through the air inlet; part of the air can be ejected from the air outlet at high speed via the spray port, and the other part of the air can flow into the liquid storage tank via the air delivery tube, such that the liquid in the liquid storage tank is delivered via the liquid delivery tube to the spray port under pressure; the liquid at the spray port is dispersed and sprayed as a mist under the impact of high-speed airflow, thereby achieving the spray effect. The fogger of this utility model is fitted with a liquid storage tank in the casing, and it does not need to be connected to an external liquid delivery line during use, making the overall structure of the fogger more compact, which occupies less space; additionally, the user can freely move the fogger to a suitable position as needed, making the fogger more convenient to use.

In one of the embodiments, a one-way valve is located along the said air delivery tube, and the said one-way valve is used to control the one-way flow of air from the said air duct to the said liquid storage tank.

In one of the embodiments, the said fan includes a carbon brush motor and an impeller connected to the output end of the said carbon brush motor; an air duct pressure plate is located on the inner wall surface of the said air duct shell, the said air duct pressure plate and the said air duct shell form an enclosed air induction channel, the said air induction channel has an air intake port near the said air inlet that is connected to the said air duct, the said air duct shell has an air supply outlet that is connected to the said air induction channel, and the said air delivery tube is connected to the said air supply outlet; the said carbon brush motor is located on the side of the air duct pressure plate away from the said air induction channel, and the carbon brush of the said carbon brush motor is located on the side of the said air intake port close to the said air supply outlet.

In one of the embodiments, a tube connector segment that is connected to the said air supply outlet is located on the outer wall of the said air duct shell.

In one of the embodiments, a flow regulating valve is located along the said liquid delivery tube, and a regulating button for regulating the said flow regulating valve is located on the said casing.

In one of the embodiments, the said air duct shell includes a main body that houses the said fan and an air outlet segment that is connected to the said main body; the said air inlet is located on one side of the main body, the said air outlet is located on the side of the air outlet segment that is away from the main body, and the internal diameter of the said air outlet segment is smaller than that of the said main body.

In one of the embodiments, the said casing includes a nozzle cover that detachably sheathes the periphery of the air outlet segment, the said spray port is located on the end of the said nozzle cover opposite to the said air outlet, and the air duct assembly further includes a detachable atomizing nozzle located in the said air outlet segment.

In one of the embodiments, an outer thread is located on the outer surface of the said air outlet segment, an inner thread that matches the said outer thread is located on the inner surface of the said nozzle cover, and the said nozzle cover is screwed to the said air outlet segment.

In one of the embodiments, a nozzle fastener is located in the said air outlet segment, the said nozzle fastener includes a fastener ring, a fastener canister located in the center of the said fastener ring, and a plurality of connecting bars between the said fastener canister and the said fastener ring and an air flow channel is formed between two adjacent connecting bars; the said atomizing nozzle includes a spray tube, the said liquid delivery tube is connected to the said spray tube via the said fastener canister, and the said atomizing nozzle also has guide channels that are connected to the said air flow channels.

In one of the embodiments, the said atomizing nozzle also includes an outer ring body positioned on the periphery of the spray tube, and a plurality of guide vanes connected between the said outer ring body and the said spray tube; a guide channel is formed between two adjacent guide vanes.

In one of the embodiments, the said air duct shell includes a first half shell and a second half shell; the said first half shell and the said second half shell are detachably connected, and a clamping groove for clamping the said nozzle fastener is located on the inner wall of the said first half shell and/or the said second half shell.

DESCRIPTIONS OF DRAWINGS

Figure 5:
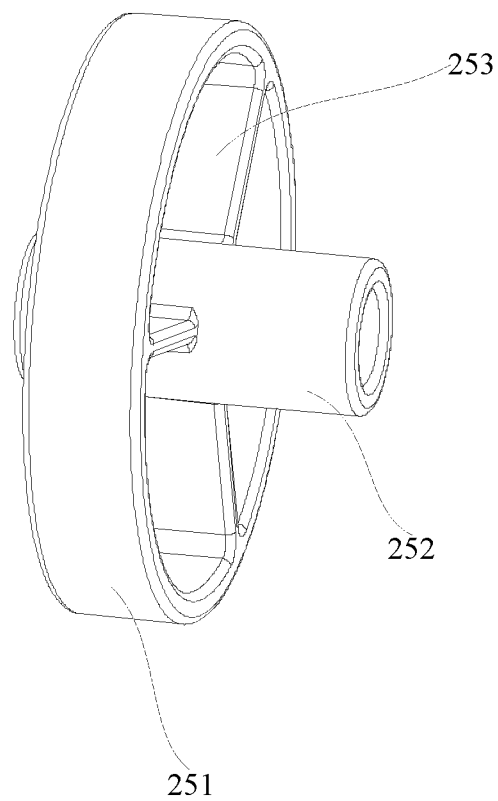

FIG. 5 is the schematic diagram of the structure of the nozzle fastener. 10, casing; 101, air suction inlet; 102, spray port; 11, regulating button; 12, nozzle cover; 20, air duct assembly; 201, air inlet; 202, air outlet; 203, air duct; 204, air supply outlet; 205, air induction channel; 206, air intake port; 207, groove; 21a, first half shell; 21b, second half shell; 211, tube connector segment; 212, main body; 213, air outlet segment; 22, fan; 221, carbon brush motor; 2211, carbon brush; 222, impeller; 23, air duct pressure plate; 24, atomizing nozzle; 241, outer ring body; 242, spray tube; 243, guide vanes; 25, nozzle fastener; 251, fastener ring; 252, fastener canister; 253, connecting bars; 30, liquid storage tank; 40, liquid delivery tube; 41, flow regulating valve; 50, air delivery tube; 51, one-way valve.

SPECIFIC EMBODIMENT(S)

In order to facilitate understanding of the present utility model, a more comprehensive description of the present utility model is provided below, with reference to the relevant appended drawings. The preferred embodiments of the present utility model are shown in the appended drawings. However, the present utility model may be realized in many different forms and is not limited to the embodiment methods described in the present text. On the contrary, the purpose of providing these embodiment methods is to facilitate a more thorough and comprehensive understanding of the disclosed content of the present utility model.

It is important to note that when a component is described as "fixed to" another component, it can either be directly fixed on another component or fixed to another component through an intermediate component. When a component is considered to be "connected to" another component, it can either be directly connected to another component or connected to another component via an intermediate component. Conversely, when a component is referred to as being "directly on" another component, there is no intermediate component. "First" and "second" as mentioned with regard to the present utility model do not represent any specific quantity or order, and are only used to distinguish names.

Figure 1:
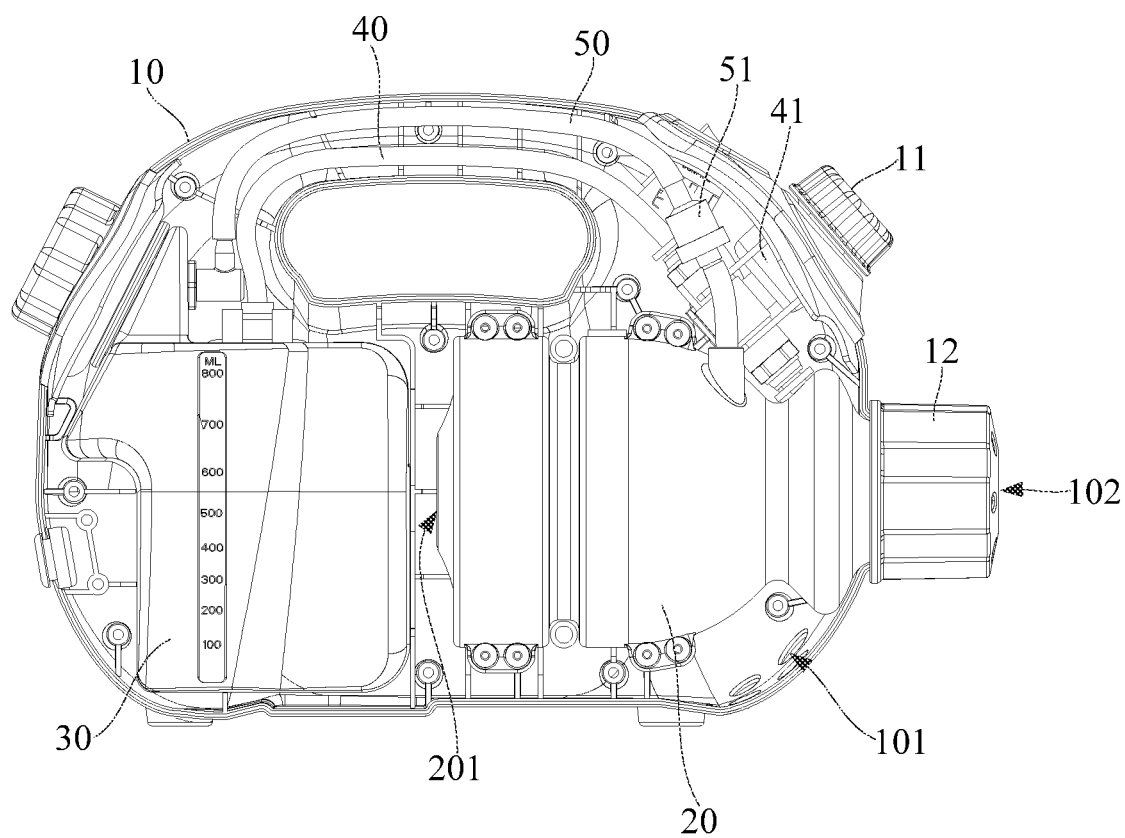
FIG. 1 is a partial sectional view of the fogger described in an embodiment of the present utility model.
Figure 2:
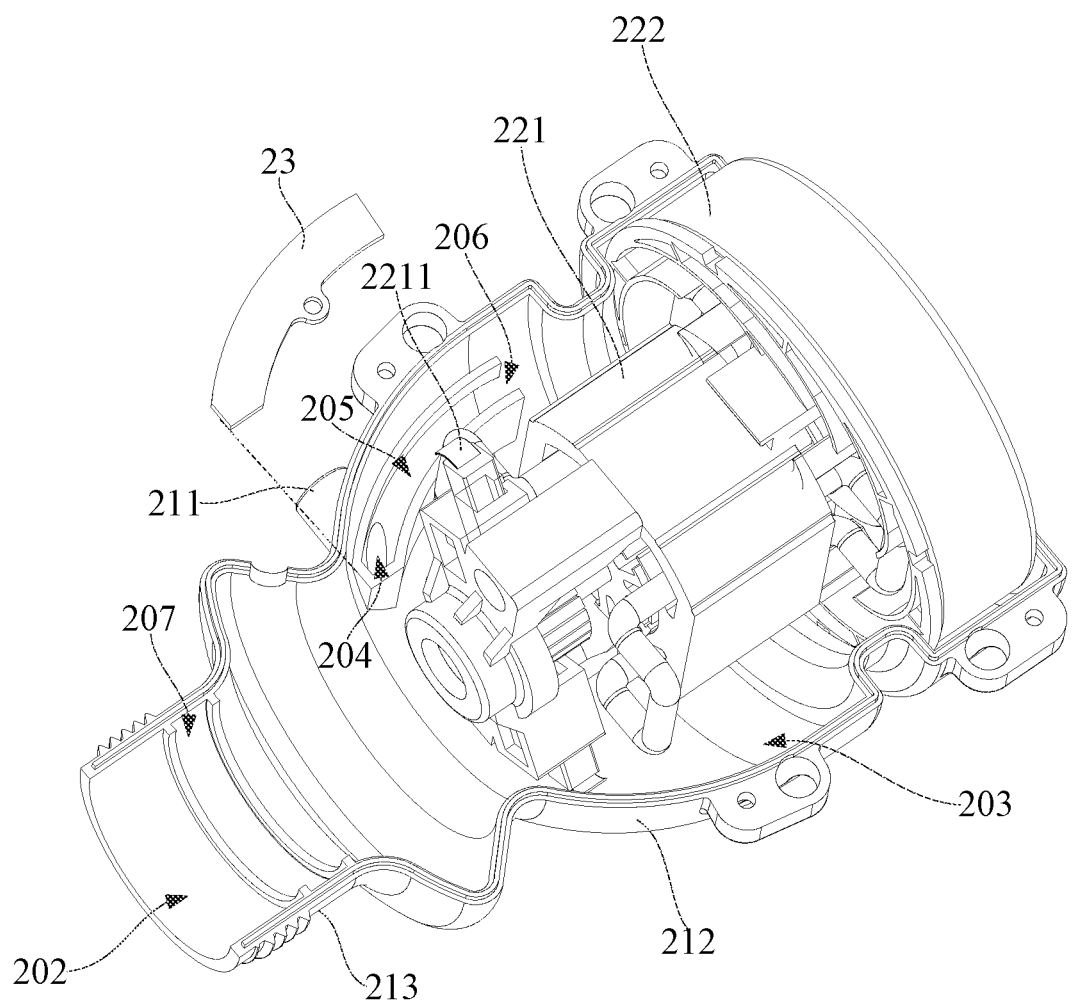
FIG. 2 is a partial sectional view of the air duct assembly.
Figure 3:
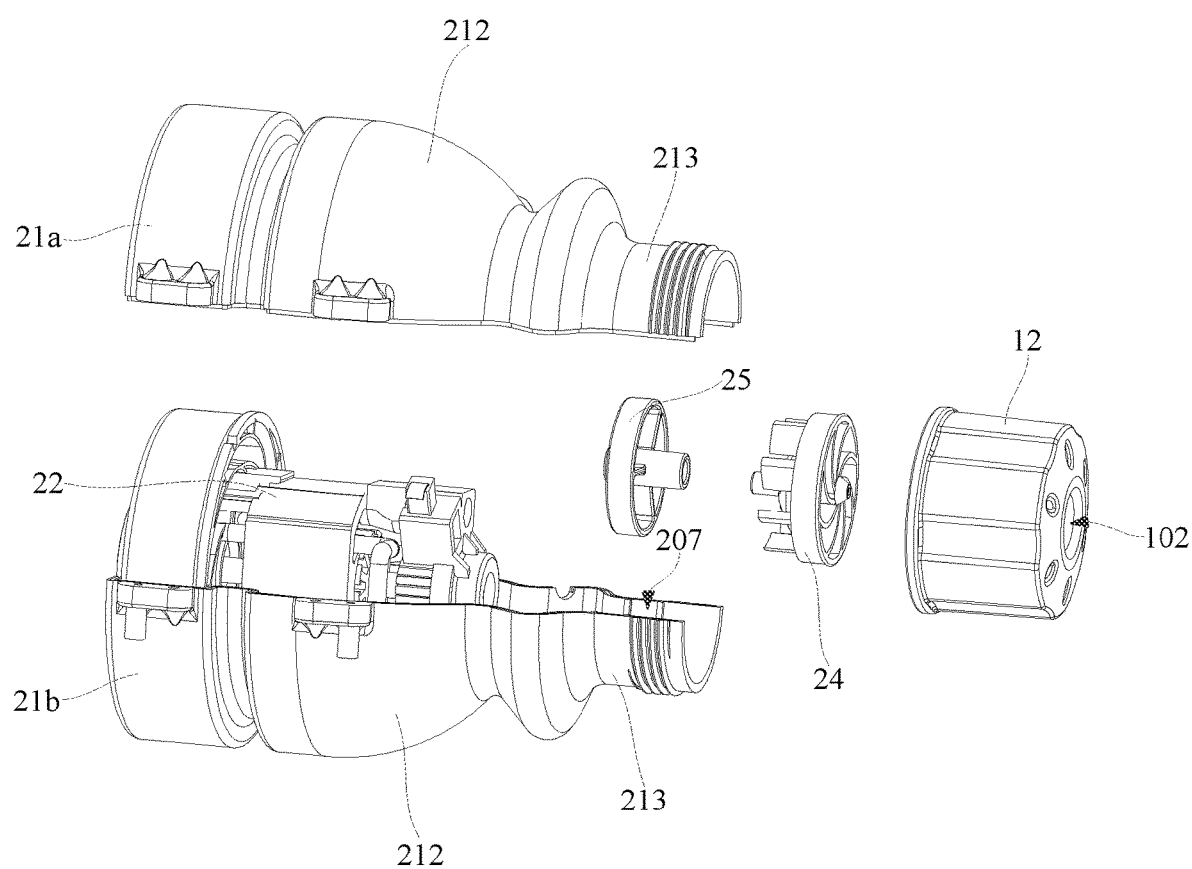
FIG. 3 shows the schematic diagram of the deconstructed structure of the air duct assembly.

Please refer to FIGS. 1 to 3 for a fogger that includes a casing 10, an air duct assembly 20 and a liquid storage tank 30. Of which, casing 10 has an air suction inlet 101 and a spray port 102; air duct assembly 20, which is located in casing 10, includes an air duct shell and fan 22, the air duct shell has an air inlet 201, an air outlet 202 and an air duct 203 that connects air inlet 201 to air outlet 202, fan 22 is located in air duct 203, air inlet 201 is connected to air suction inlet 101, and air outlet 202 is connected to spray port 102; liquid storage tank 30, which is located in casing 10, delivers liquid to spray port 102 via liquid delivery tube 40, and air duct 203 is connected to liquid storage tank 30 via air delivery tube 50.

Specifically, as shown in FIG. 1, casing 10 has a chamber for installing liquid storage tank 30 and air duct assembly 20; liquid storage tank 30 can be used to contain an aqueous solution or other disinfectant liquid, and a liquid filling port that is connected to liquid storage tank 30 is located on casing 10 to facilitate the timely replenishment of the liquid in liquid storage tank 30. As shown in FIGS. 2 and 3, air duct assembly 20 includes an air duct shell and fan 22, wherein the air duct shell is used to form air duct 203, and fan 22 generates a certain negative pressure during operation that sucks air from the outside into air duct 203, with part of the air entering liquid storage tank 30 via air delivery tube 50.

The aforementioned fogger uses fan 22 to suck air from the outside into casing 10 via air suction inlet 101, and the air flows into air duct 203 through air inlet 201. Part of the air can be ejected from air outlet 202 at high speed via spray port 102, and the other part of the air can flow into liquid storage tank 30 via air delivery tube 50, such that the liquid in liquid storage tank 30 is delivered via liquid delivery tube 40 to spray port 102 under pressure; the liquid at spray port 102 is dispersed and sprayed as a mist under the impact of high-speed air flow, thereby achieving a spray effect. The fogger of the present utility model is fitted with liquid storage tank 30 in casing 10, and it does not need to be connected to an external liquid delivery line during use. This makes the overall structure of the fogger more compact and it occupies less space. In addition, the user can freely move the fogger to a suitable location as needed, making the fogger more convenient to use.

In one of the embodiments, one-way valve 51 is located along air delivery tube 50, and one-way valve 51 is used to control the one-way flow of air from air duct 203 to liquid storage tank 30. Specifically, one-way valve 51 is located along air delivery tube 50; when air flows from air duct 203 to liquid storage tank 30, one-way valve 51 opens to connect air duct 203 with liquid storage tank 30, ensuring that the air flows through, and when liquid in liquid storage tank 30 flows back, one-way valve 51 is in a closed state, which cuts off liquid storage tank 30 from air duct 203 and prevents liquid from entering air duct 203. As air delivery tube 50 is fitted with one-way valve 51, liquid in liquid storage tank 30 can be prevented from flowing back from air delivery tube 50 into air duct 203, which effectively prevents water from flowing to fan 22, and thus effectively improves the service life and usage safety of the fogger.

Please refer to FIG. 2. In one of the embodiments, fan 22 includes carbon brush motor 221 and impeller 222 that is connected to the output end of carbon brush motor 221; air duct pressure plate 23 is located on the inner wall surface of the air duct shell, and air duct pressure plate 23 and the air duct shell form the enclosed air induction channel 205, air induction channel 205 has air intake port 206 near air inlet 201 that is connected to air duct 203; the air duct shell has air supply outlet 204 that is connected to air induction channel 205, air delivery tube 50 is connected to air supply outlet 204, carbon brush motor 221 is located on the side of air duct pressure plate 23 away from air induction channel 205, and carbon brush 2211 of carbon brush motor 221 is located on the side of air intake port 204 close to air supply outlet 206.

In the present embodiment, carbon brush motor 221 works to drive the rotation of impeller 222 and thereby achieve the effect of guiding the air; air duct pressure plate 23 and the air duct shell form the enclosed air induction channel 205; for the convenience of explanation, air duct pressure plate 23 in FIG. 2 is in an open state; during normal operations, air duct pressure plate 23 covers the side of air induction channel 205, and a part of the air flow in air duct 203 may flow into air induction channel 205 from air intake port 206, and then flow into air delivery tube 50 from air supply outlet 204. As carbon brush motor 221 will generate a certain amount of carbon dust during operation, the inclusion of air duct pressure plate 23 is able to separate carbon brush motor 221 from air induction channel 205; additionally, carbon brush 2211 of carbon brush motor 221 is on the side of air intake port 206 that is close to air supply outlet 204, as such, air entering from air intake port 206 will not carry carbon dust generated by carbon brush 2211, and this would effectively prevent carbon dust from being sucked into air delivery tube 50 and thereby clog air delivery tube 50. When one-way valve 51 is placed on air delivery tube 50, the aforementioned design can also prevent carbon dust from clogging one-way valve 51, which would result in its failure.

In addition, in order to facilitate the installation of air delivery tube 50, the outer wall of the air duct shell is fitted with a tube connector segment 211 that is connected to air supply outlet 204; during assembly, air delivery tube 50 just needs to be inserted into tube connector segment 211, allowing for simple and convenient operation.

Please refer to FIG. 1. In one of the embodiments, flow regulating valve 41 is positioned on liquid delivery tube 40, and regulating button 11 that is used to adjust flow regulating valve 41 is positioned on casing 10. During use, the user can adjust flow regulating valve 41 through regulating button 11 to adjust the liquid flow in liquid delivery tube 40, so as to achieve different atomization effects, allowing for simple and convenient operation.

Please refer to FIGS. 2 and 3. In one of the embodiments, the air duct shell includes main body 212 that is used to house fan 22 and air outlet segment 213 that is connected to main body 212; air inlet 201 is located on one side of main body 212, air outlet 202 is located on the side of air outlet segment 213 that is away from main body 212, and the internal diameter of air outlet segment 213 is smaller than that of main body 212. Under the action of the fan 22, air first enters main body 212 from air inlet 201, then flows from main body 212 to air outlet segment 213, and is finally expelled from air outlet 202 of air outlet segment 213. Since the internal diameter of air outlet segment 213 is smaller than the internal diameter of main body 212, pressure is increased to a certain extent when air flows into air outlet segment 213; this increases air flow velocity and thereby increases the force of the impact on the liquid, improving the atomization effect.

Further, please refer to FIGS. 1 and 3, casing 10 includes nozzle cover 12 that detachably sheathes the periphery of air outlet segment 213; spray port 102 is located on the end of nozzle cover 12 opposite to air outlet 202, and air duct assembly 20 further includes detachable atomizing nozzle 24 located in air outlet segment 213. Of these, nozzle cover 12 can be detachably connected and fixed to air outlet segment 213 by means of a snap-fit connection, a threaded connection or a screw connection. When atomizing nozzle 24 is clogged, nozzle cover 12 can be removed, and atomizing nozzle 24 can then be detached, so that atomizing nozzle 24 can be cleaned and cleared out to prevent the spraying effect from being affected.

Preferably, an outer thread is located on the outer surface of air outlet segment 213, an inner thread that matches the outer thread is located on the inner surface of nozzle cover 12, and nozzle cover 12 is screwed to air outlet segment 213. Nozzle cover 12 can be disassembled and assembled by screwing, allowing for simple and convenient operation.

Figure 4:
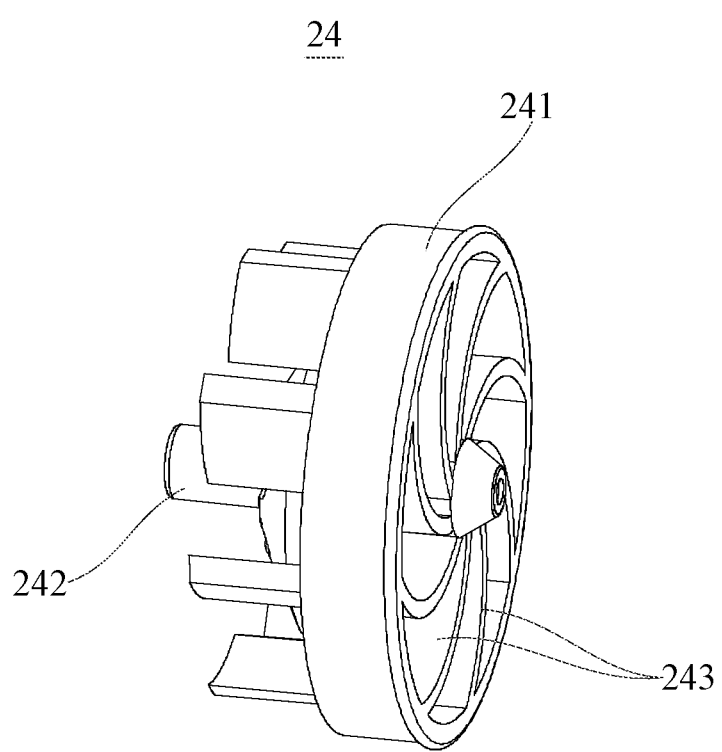
FIG. 4 is the schematic diagram of the structure of the atomizing nozzle.

Further, please refer to FIGS. 3 to 5, nozzle fastener 25 is located in air outlet segment 213; nozzle fastener 25 includes fastener ring 251, fastener canister 252 located in the center of fastener ring 251, and a plurality of connecting bars 253 between fastener canister 252 and fastener ring 251, and an air flow channel is formed between two adjacent connecting bars 253; atomizing nozzle 24 includes spray tube 242, liquid delivery tube 40 is connected to spray tube 242 via fastener canister 252, and atomizing nozzle 24 also has guide channels that are connected to the said air flow channels.

During assembly, the liquid delivery end of liquid delivery tube 40 is inserted into one end of fastener canister 252, spray tube 242 of atomizing nozzle 24 is inserted into the other end of fastener canister 252, and the nozzle cap is then connected and fixed to air outlet segment 213 to fix atomizing nozzle 24 within air outlet segment 213, allowing for simple and convenient operation. The inclusion of nozzle fastener 25 allows liquid delivery tube 40 to be conveniently connected to atomizing nozzle 24, and the liquid output from liquid delivery tube 40 can be sprayed to spray port 102 via atomizing nozzle 24; at the same time, air in air duct 203 can be delivered to spray port 102 via the air flow channels and the guide channels in sequence; under the impact of the air flow, the liquid at spray port 102 can be dispersed into mist droplets, and a better atomization effect can be achieved.

Further, as shown in FIG. 4, atomizing nozzle 24 also includes outer ring body 241 disposed on the periphery of spray tube 242, and a plurality of guide vanes 243 connected between outer ring body 241 and spray tube 242; a guide channel is formed between two adjacent guide vanes 243. Guide vanes 243 can achieve a better guide effect on the air flow, thereby further improving the atomization effect.

In addition, in an embodiment as shown in FIG. 3, the air duct shell includes first half shell 21a and second half shell 21b; first half shell 21a and second half shell 21b are detachably connected, and groove 207 for clamping and fixing nozzle fastener 25 is located on the inner wall of first half shell 21a and/or second half shell 21b. Specifically, first half shell 21a and second half shell 21b can be detachably connected by means of a snap-fit connection or a screw connection. For example, both first half shell 21a and second half shell 21b may be fitted with groove 207; during assembly, nozzle fastener 25 is first clamped to groove 207 of first half shell 21a, and second half shell 21b is then connected and fixed to first half shell 21a to realize the fixing of the nozzle fastener 25, allowing for simple and convenient operation.

The various technical features of the said embodiments above can be combined arbitrarily. In order to keep the description concise, not all possible combinations of the various technical features in the said embodiments have been described. However, as long as there is no incompatibility in the combinations of these technical features, they should be deemed to be within the scope recorded in this Specification.

The above embodiment is merely illustrative of several embodiment methods of the present utility model; while its description is relatively specific and detailed, it is not to be construed as limiting the scope of the utility model patent. It should be noted that a number of variations and modifications may be made by those skilled in the art without departing from the spirit and scope of the present utility model, and these shall fall within the scope of protection of the present utility model patent. Hence, the protection scope of the present utility model patent should be based on the attached Claims.

The invention claimed is:

1. A fogger, wherein, the fogger comprises:
a casing with an air suction inlet and a spray port;
an air duct assembly located in the said casing, wherein the air duct assembly includes an air duct shell and a fan, of which the said air duct shell has an air inlet, an air outlet, and an air duct that connects the said air inlet and the said air outlet, and the said fan is located in the air duct; the said air inlet is connected to the said air suction inlet, the said air outlet is connected to the said spray port;

a liquid storage tank located in the said casing, wherein the liquid storage tank delivers liquid to the said spray port via a liquid delivery tube, and the said air duct is connected to the liquid storage tank via an air delivery tube; and wherein a one-way valve is located along the said air delivery tube, and the said one-way valve is used to control the one-way flow of air from the said air duct to the said liquid storage tank.

2. The fogger as claimed in claim 1, wherein the said fan includes a carbon brush motor, an impeller connected to the output end of the carbon brush motor; an air duct pressure plate is located on the inner wall surface of the said air duct shell, and the said air duct pressure plate and the said air duct shell form an enclosed air induction channel; the said air induction channel has an air intake port near the said air inlet that is connected to the said air duct, the said air duct shell has an air supply outlet that is connected to the said air induction channel; the said air delivery tube is connected to the said air supply outlet, the said carbon brush motor is located on the side of the air duct pressure plate away from the said air induction channel, and the carbon brush of the said carbon brush motor is located on the side of the said air intake port close to the said air supply outlet.

3. The fogger as claimed in claim 2, wherein a tube connector segment that is connected to the said air supply outlet is located on the outer wall of the said air duct shell.

4. The fogger as claimed in claim 1, wherein a flow regulating valve is located along the said liquid delivery tube, and a regulating button for regulating the said flow regulating valve is located on the said casing.

5. The fogger as claimed in claim 1, wherein the said air duct shell includes a main body that houses the said fan and an air outlet segment that is connected to the said main body; the said air inlet is located on one side of the main body, the said air outlet is located on the side of the air outlet segment that is away from the main body, and the internal diameter of the said air outlet segment is smaller than that of the said main body.

6. The fogger as claimed in claim 5, wherein the said casing includes a nozzle cover that detachably sheathes the periphery of the air outlet segment; the said spray port is located on the end of the said nozzle cover opposite to the said air outlet, and the air duct assembly further includes a detachable atomizing nozzle located in the air outlet segment.

7. The fogger as claimed in claim 6, wherein an outer thread is located on the outer surface of the said air outlet segment, an inner thread that matches the said outer thread is located on the inner surface of the said nozzle cover, and the said nozzle cover is screwed to the said air outlet segment.

8. The fogger as claimed in claim 6, wherein a nozzle fastener is located in the said air outlet segment; the said nozzle fastener includes a fastener ring, a fastener canister located in the center of the fastener ring, and a plurality of connecting bars between the said fastener canister and the said fastener ring, and air flow channels are formed between every two adjacent connecting bars; the said atomizing nozzle includes a spray tube, the said liquid delivery tube is connected to the said spray tube via the said fastener canister, and the said atomizing nozzle also has guide channels that are connected to the said air flow channels.

9. The fogger as claimed in claim 8, wherein the said atomizing nozzle also includes an outer ring body positioned on the periphery of the spray tube, and a plurality of guide vanes connected between the outer ring body and the spray tube; guide channels are formed between every two adjacent guide vanes.

10. The fogger as claimed in claim 8, wherein the said air duct shell includes a first half shell and a second half shell; the first half shell and the second half shell are detachably connected, and a clamping groove for clamping the said nozzle fastener is located on the inner wall of the said first half shell and/or said second half shell.

\* \* \* \* \*